United States Patent
Schapiro et al.

(10) Patent No.: US 8,967,378 B2
(45) Date of Patent: Mar. 3, 2015

(54) HANDHELD TOOTHPASTE DISPENSING SYSTEM

(76) Inventors: Edward Schapiro, Boca Raton, FL (US); Daniel M. Schapiro, Boca Raton, FL (US); Michelle Bacarella, Gilbert, AZ (US); Tom Ingolia, Morton, IL (US); Steve Rittmanic, Chandler, AZ (US)

(*) Notice: Subject to any disclaimer, the term of this patent is extended or adjusted under 35 U.S.C. 154(b) by 422 days.

(21) Appl. No.: 13/447,891

(22) Filed: Apr. 16, 2012

(65) Prior Publication Data
US 2012/0261300 A1    Oct. 18, 2012

Related U.S. Application Data

(60) Provisional application No. 61/475,297, filed on Apr. 14, 2011.

(51) Int. Cl.
| | | |
|---|---|---|
| *B65D 83/10* | (2006.01) | |
| *A61K 8/73* | (2006.01) | |
| *A61Q 11/00* | (2006.01) | |
| *A61K 8/34* | (2006.01) | |
| *A61K 8/86* | (2006.01) | |
| *A61K 8/97* | (2006.01) | |
| *A61K 8/19* | (2006.01) | |

(52) U.S. Cl.
CPC . *A61K 8/73* (2013.01); *A61Q 11/00* (2013.01); *A61K 8/345* (2013.01); *A61K 8/86* (2013.01); *A61K 8/97* (2013.01); *A61K 8/19* (2013.01); *A61K 2800/87* (2013.01)
USPC .............................. 206/369; 206/533; 221/87

(58) Field of Classification Search
USPC ........ 206/63.5, 368, 369, 528, 530, 531, 533, 206/538, 539; 132/308; 221/25, 75, 86, 87, 221/88, 89, 197, 287; 401/132; 424/49
See application file for complete search history.

(56) References Cited

U.S. PATENT DOCUMENTS

| | | | | |
|---|---|---|---|---|
| 4,307,734 A * | 12/1981 | Blankenship | .................. | 206/533 |
| 5,322,166 A * | 6/1994 | Crowther | ...................... | 206/538 |
| 5,664,697 A * | 9/1997 | Lambelet et al. | ................ | 221/89 |
| 5,799,821 A * | 9/1998 | Lambelet et al. | ................ | 221/86 |
| 6,098,835 A * | 8/2000 | DeJonge | ........................ | 206/531 |
| 6,364,155 B1 * | 4/2002 | Wolfe | .............................. | 221/25 |
| 6,669,022 B2 * | 12/2003 | Donegan | ....................... | 206/531 |
| 2010/0300921 A1 * | 12/2010 | Scholer | .......................... | 206/528 |
| 2013/0029294 A1 * | 1/2013 | Schapiro et al. | ................ | 424/58 |

* cited by examiner

*Primary Examiner* — Luan K Bui
(74) *Attorney, Agent, or Firm* — Robert M. Downey, P.A.

(57) ABSTRACT

A handheld toothpaste dispensing system that dispenses single serving portions of toothpaste in preformed shapes includes an outer housing surrounding an interior chamber. To load the dispensing system, a replaceable or refillable disk containing single serving portions of toothpaste assembled in spaced arrangement is inserted into the interior chamber of the dispensing device and is supported on a disk advancing mechanism. In operation, a button on the dispensing device is pressed to operate the disk advancing mechanism, thereby advancing the disk through a partial rotational movement and exposing the subsequent compartment on the disk within a dispensing opening on the housing of the device. The preformed shapes of toothpaste are removed from the disk for brushing by inserting the bristles of the user's toothbrush into the preformed shape of toothpaste and subsequently pulling the toothbrush away from the disk with the single serving toothpaste shape clinging to the bristles.

3 Claims, 7 Drawing Sheets

HANDHELD TOOTHPASTE DISPENSING SYSTEM

This patent application is based on provisional patent application Ser. No. 61/475,297 filed on Apr. 14, 2011.

BACKGROUND OF THE INVENTION

1. Field of the Invention

The present invention relates to toothpaste for brushing one's teeth and, more particularly, a toothpaste dispensing system that dispenses single serving portions of toothpaste in preformed shapes.

2. Discussion of the Related Art

Toothpaste is a paste or gel used to clean and improve the health and aesthetic appearance of teeth. Used in conjunction with a toothbrush, toothpaste promotes oral hygiene by aiding the removal of dental plaque and food from the teeth, and often includes fluoride for prevention of tooth and gum disease.

Toothpaste is typically stored within a cavity of a handheld container, which may be squeezed by a user to force the toothpaste outwards through an opening in communication with the cavity. The user must continue to squeeze the handheld container until the desired amount of toothpaste has been emitted onto the user's toothbrush and the user can begin brushing his or her teeth.

It is frequently a difficult task for parents and caregivers to teach young children the importance of oral hygiene, as children often lack the patience required by tooth brushing. This is due in part to the fact that tooth brushing is a rather monotonous activity that fails to capture the interest of young children. This problem is further due to the difficulty encountered by young children associated with the process of properly dispensing toothpaste onto a toothbrush. Children are prone to dispensing too much or too little toothpaste onto their toothbrush. Moreover, children often make a mess when trying to control the toothpaste container in one hand and the toothbrush in the other hand while trying to squeeze toothpaste onto the toothbrush.

A number of inventions intended for children have been directed towards simplifying the preparation process associated with tooth brushing. One example is the combination toothbrush and toothpaste dispenser disclosed in U.S. Pat. No. 7,527,446 to Johnson Papa et al. The '446 apparatus includes a dispenser housing that is sized to hold a toothpaste cartridge. The dispenser housing includes an activator button which, when pressed with downward force, forces toothpaste out of an orifice and onto the user's toothbrush. While the '446 apparatus is useful for its intended purpose, its bulky size is inconvenient. Furthermore, the '446 apparatus is sufficiently dissimilar to a traditional handheld toothpaste dispenser such that children do not become familiar with the conventional process of putting toothpaste onto a toothbrush. Therefore, there remains a need for a toothpaste dispensing system that provides single serving portions of toothpaste in preformed shapes, which can be easily operated by young children.

OBJECTS AND ADVANTAGES OF THE INVENTION

Considering the foregoing, it is a primary object of the present invention to provide a toothpaste dispensing system that dispenses single serving portions of toothpaste in preformed shapes.

It is a further object of the present invention to provide a toothpaste dispensing system that is easily operable by young children.

It is a further object of the present invention to provide a toothpaste dispensing system that encourages young children to brush their teeth by providing toothpaste dispensing systems that are appealing to young children.

It is a further object of the present invention to provide a toothpaste dispensing system that includes single servings of toothpaste which can be easily picked up by pushing the bristles of a toothbrush into the preformed shape of toothpaste.

It is a further object of the present invention to provide a toothpaste dispensing system that includes preformed shapes of toothpaste that are formed into shapes that are appealing to young children.

It is still a further object of the present invention to provide a toothpaste dispensing system that prevents young children from making a mess while preparing to brush their teeth.

It is yet a further object of the present invention to provide a toothpaste dispensing system that prevents waste of toothpaste.

These and other objects and advantages of the present invention are more readily apparent with reference to the detailed description and accompanying drawings.

SUMMARY OF THE INVENTION

The present invention is directed to a handheld toothpaste dispensing system that dispenses single serving portions of toothpaste in preformed shapes and is easily operable by young children. The system includes a dispensing device that has a disk advancing mechanism designed to be operable within a housing that may be held in a child's hand and is ideally designed to appeal to young children. The system also includes replaceable or refillable disks containing single serving portions of toothpaste provided in preformed shapes and contained in cups or compartments that are arranged at spaced intervals about an outer circumferential zone of the disk. The disks are designed to be individually placed within the dispensing device. In operation, a button on the dispensing device is pressed, thereby advancing the disk within the handheld toothpaste dispensing system and exposing the subsequent compartment on the disk through an opening on the handheld device. The preformed shapes of toothpaste may be removed from the disk for use by inserting the bristles of the user's toothbrush through the opening of the device and into contact with the preformed shape of toothpaste, and then subsequently pulling the toothbrush away from the disk. In a preferred embodiment, each compartment containing a single serving of toothpaste is covered by a protective foil film that is peeled open to expose the preformed shape of toothpaste just prior to removal.

DESCRIPTION OF THE DRAWINGS

For a fuller understanding of the nature of the present invention, reference should be made to the following detailed description taken in conjunction with the accompanying drawings in which.

Like reference numerals refer to like referenced parts throughout the several views of the drawings.

DETAILED DESCRIPTION OF THE PREFERRED EMBODIMENTS

Referring to the several views of the drawings, the handheld toothpaste dispensing system that dispenses single serving portions of toothpaste in preformed shapes is shown according to the several embodiments of the invention and is generally indicated as 10.

Figure 1:
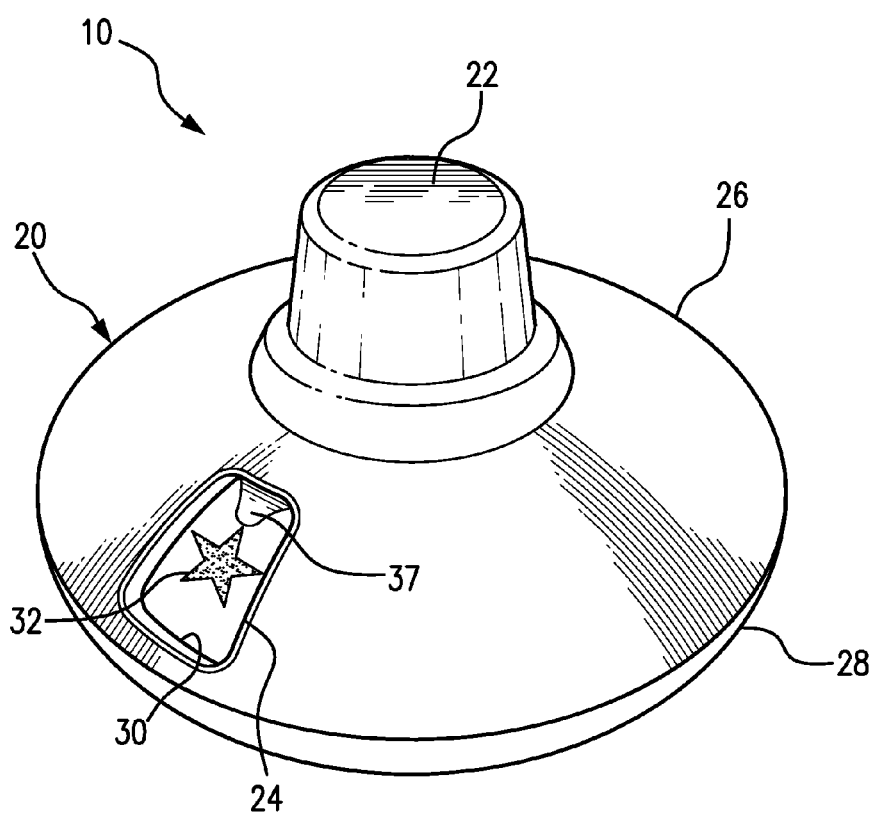
FIG. 1 is a perspective view illustrating the handheld toothpaste dispensing system of the present invention, in accordance with one embodiment.
Figure 2:
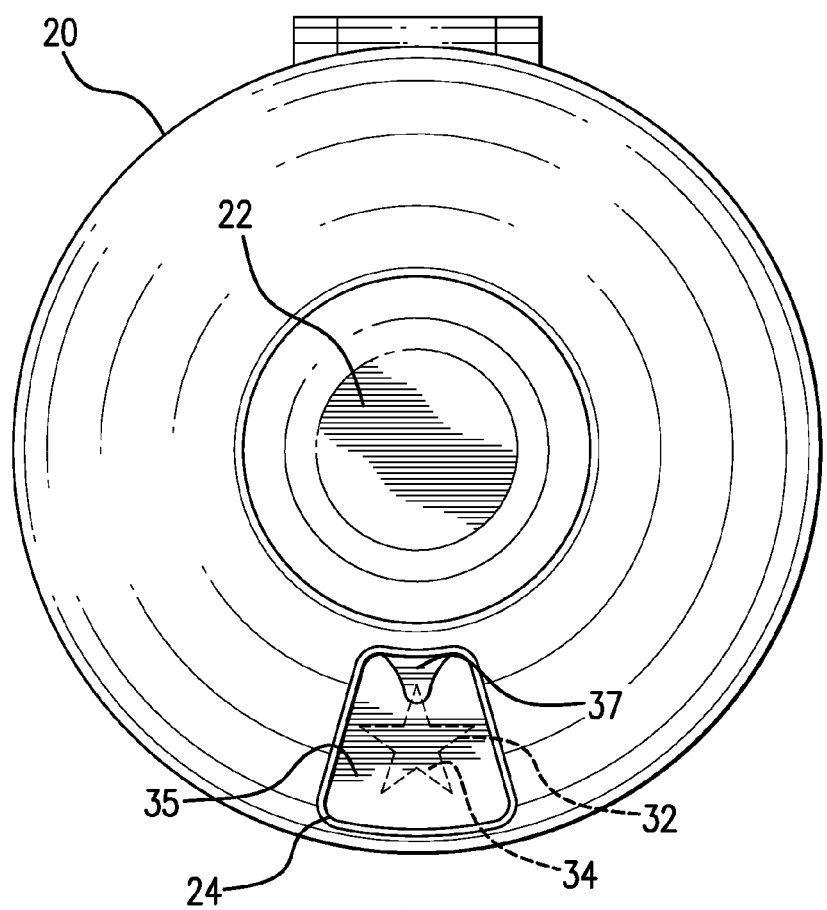
FIG. 2 is a top plan view illustrating the handheld toothpaste dispensing system of the present invention, in accordance with one embodiment.
Figure 3:
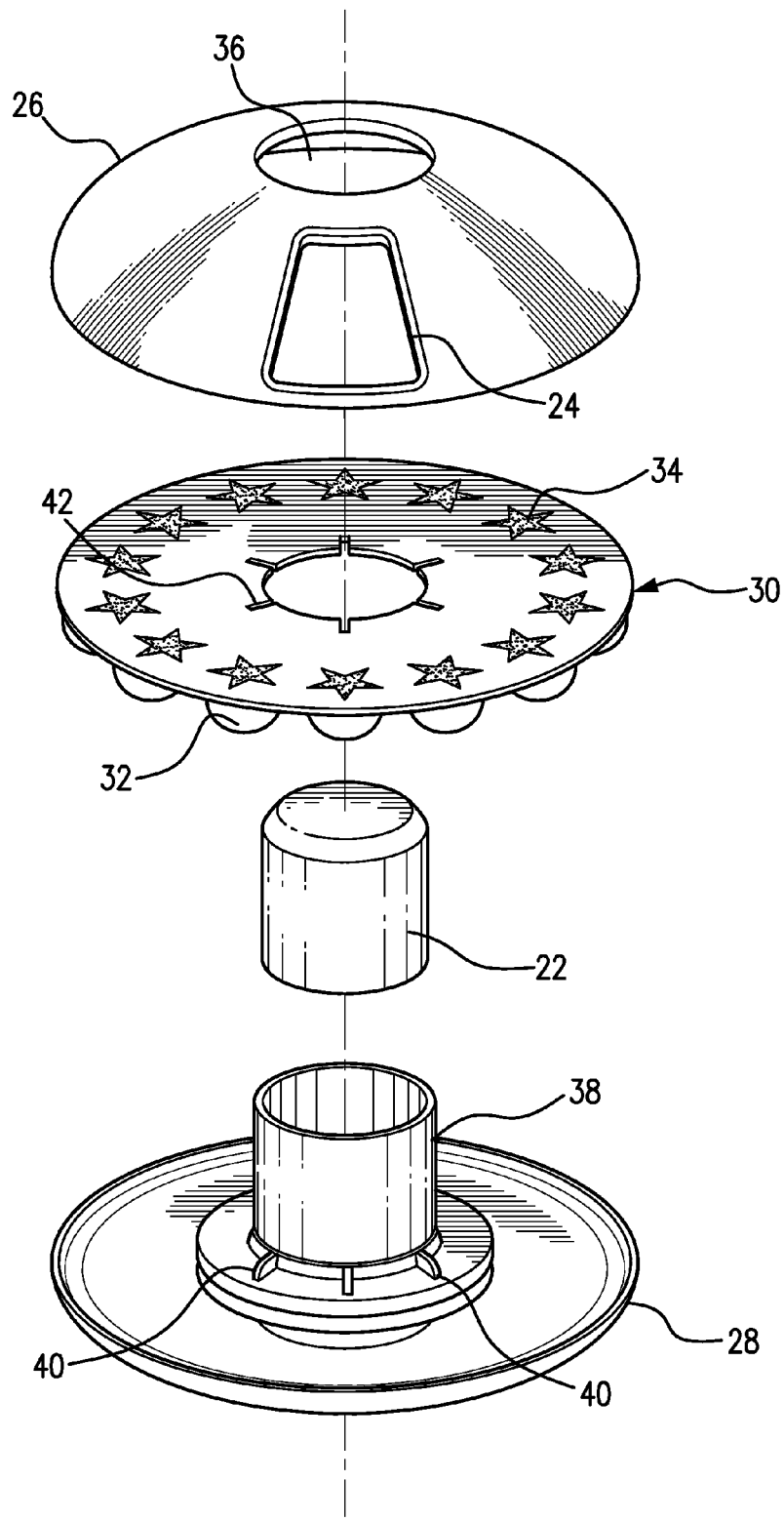
FIG. 3 is an exploded view of the handheld toothpaste dispensing system illustrating an upper component, a disk containing single serving portions of toothpaste in preformed shapes, an internal disk advancing mechanism, and a lower component, in accordance with one embodiment.
Figure 4:
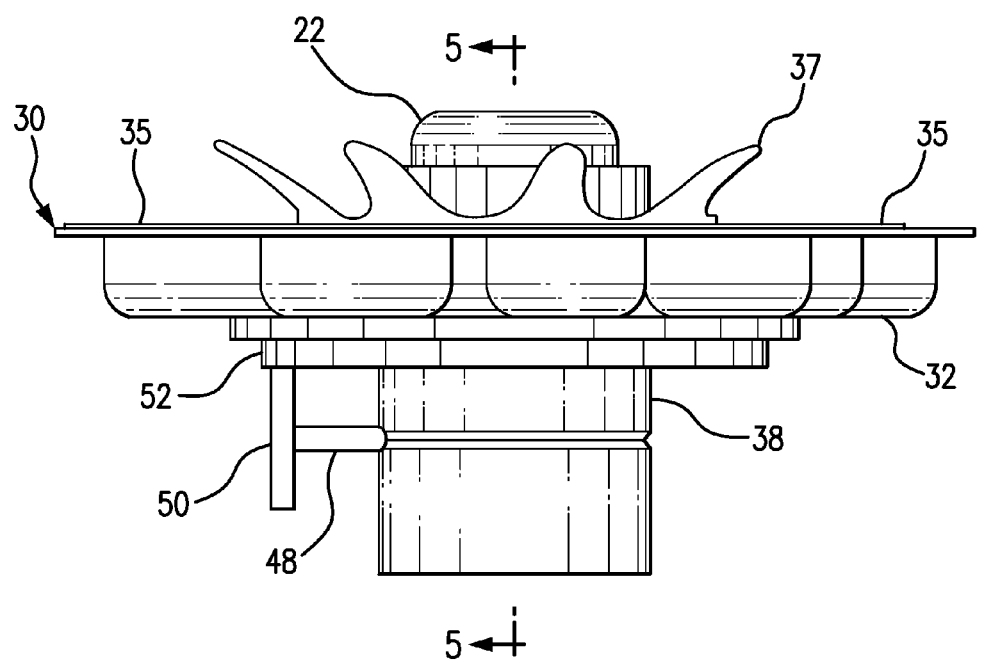
FIG. 4 is a side view of the internal disk advancing mechanism and a disk having single serving toothpaste compartments covered by removable protective films that have pull tabs.
Figure 5:
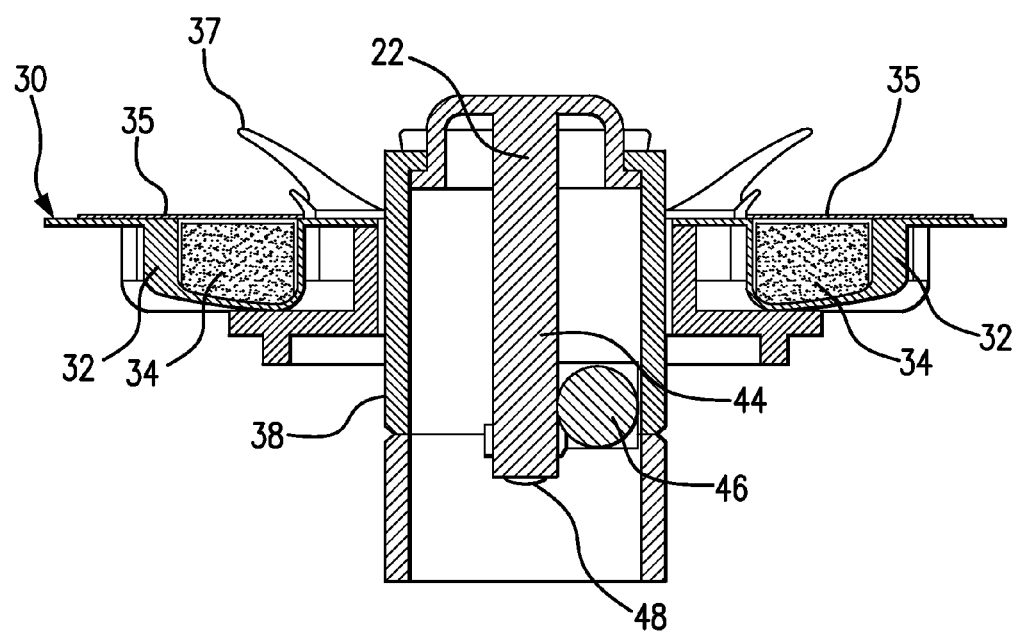
FIG. 5 is a side view of the internal disk advancing mechanism, shown in cross-section, taken from the line 5-5 in FIG. 4.
Figure 6:
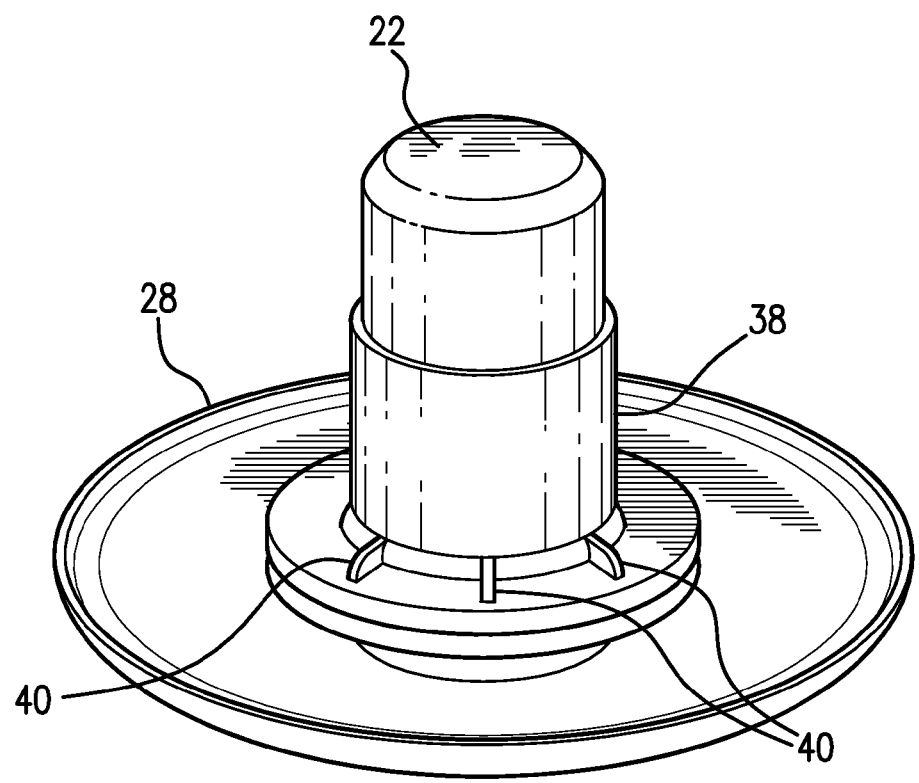
FIG. 6 is a perspective view of the lower compartment with the disk advancing mechanism.

Referring generally to FIGS. 1 and 2, the dispensing system 10 includes a handheld dispensing device 20 that has an outer housing. The handheld dispensing device 20 includes an upper component 26 and a lower component 28 sized for releasably locking together to form an interior chamber. A disk advancing mechanism 38 is located within the interior chamber and is operable using a depressible button 22 on the handheld dispensing device 20. The dispensing device 20 housing is structured for being grasped within a user's hand in a position that allows the user's thumb to depress the button 22 in order to operate the disk advancing mechanism 38. A circular disk 30 having cups or compartments 32 arranged at spaced intervals about an outer circumferential zone 33 of the disk 30 for storing preformed single servings 34 of toothpaste is sized for insertion between the upper and lower components 26 and 28. Each compartment 30 includes a protective film cover 35 with a pull tab 37. The film cover serves to maintain the freshness of the single serving 34 of toothpaste stored therein. Ideally, at least some air space is maintained between each of the film covers 35 and each of the single servings 34 of toothpaste contained in the compartment 32 below the film cover 35.

The button 22 is included on the top side of the lower component 28 for operating the disk advancing mechanism 38. An opening 36 on the upper component 26 is sized for passage of the button 22 therethrough when the upper and lower compartments 26, 28 are closed, as seen in FIGS. 1 and 2. The upper component 26 has a window or opening 24 for exposing a single compartment 32 on the disk 30 and accessing a single serving 34 of toothpaste using the bristles of a user's toothbrush. The opening 24 is sized for insertion of a user's fingers (e.g. the thumb and index finger) for grasping the tab 37 and removing the protective film cover 35 from the compartment 32 just prior to dispensing of the preformed single serving 34 of toothpaste stored therein. Each compartment 32 may be shaped to coincide with the pre-formed shape of the single serving of toothpaste.

In order to insert a disk 30 into the dispensing device 20, the upper and lower components 26 and 28 are separated. The upper component and lower components 26 and 28 may be hingedly connected or, alternatively, screw-tight connectable. Other methods of releasably locking the components 26 and 28 together that are suitable may be used as well. Ideally, the releasable locking mechanism is uncomplicated so that a child can easily replace a disk without the aid of an adult.

Referring to FIGS. 3-6, the internal disk advancing mechanism 38 includes ribs 40 that line up with open slots 42 located on bottom face of the disk 30 for interlocking the disk 30 with the disk advancing mechanism 38 to ensure that the disk 30 stays in place and maintains proper registered positioning relative to the dispensing opening 24 during use. In operation, when the button 22 on the dispensing system 10 is pressed down, forcing button shaft 44 down, a slider gear 46 is moved against transmission gear 48 that is mounted to the button shaft 44, causing transmission gear 48 to be momentarily rotated. Rotation of the transmission gear 48 causes a rotator gear 50 to drivingly rotate a crown gear 52, which in turn advances the disk 30 in a partial rotating motion relative to the dispensing device 20, thereby exposing the subsequent compartment 32 on the disk 30 through the dispensing opening 24 on the upper component 28. After being pressed down, the button 22 automatically returns to its original, raised position. This may be achieved with the use of an internal spring or other biasing element.

Figure 7:
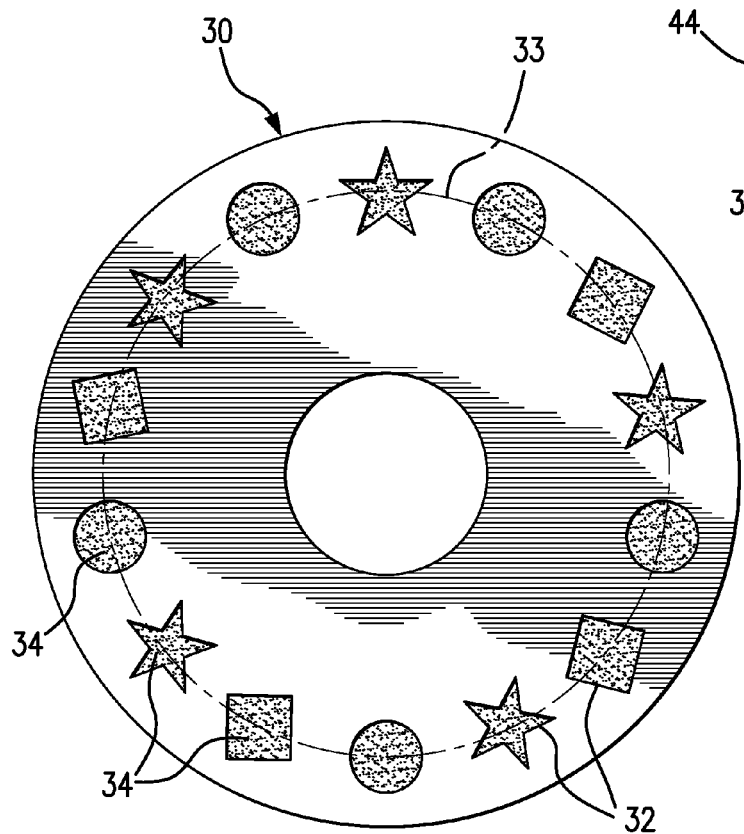
FIG. 7 is a top plan view of a disk with the single servings of toothpaste in preformed shapes contained in the spaced compartments.

Referring to FIG. 7, a preferred embodiment of the disk 30 is shown. The single servings 34 of toothpaste are manufactured in preformed shapes and include an outer shell that preserves the freshness of the preformed shape until the user puts the single serving 34 into his or her mouth and begins brushing his or her teeth, which causes the outer shell to dissolve, thereby allowing the user to apply the toothpaste to all of his or her teeth. The single servings 34 of toothpaste in preformed shapes may be removed from the disk 30 for use by penetrating the outer surface of a single serving 34 using the bristles of the user's toothbrush and subsequently pulling the toothbrush away from the disk 30. The single serving 34 of toothpaste clings to the bristles of the toothbrush prior to the brushing process and contains the approximate amount of toothpaste required to adequately brush one's teeth a single time, thereby significantly reducing the likelihood of a child creating a mess while brushing. Ideally, the single servings 34 are preformed into shapes, such as stars, which are appealing to young children.

The single servings 34 of toothpaste in preformed shapes are particularly formulated and structured to cling to the bristles of a user's toothbrush to aid in the removal of the single serving 34 from a compartment 32 and maintaining its form prior to use (i.e. placement within a user's mouth). Upon entering the user's mouth, the single serving 34 dissolves into a spreadable paste having traditional toothpaste-like consistency. A preferred formulation of the single servings 34 of toothpaste in preformed shapes includes the following ingredients:

| Ingredients | Percentage by Weight of in the Composition |
| --- | --- |
| Konjac Gum | 1-3% |
| Tara Gum | 0.5-1.1% |
| Xanthum/Guar Gum | 0.15-0.35% |
| Polyethylene Glycol-3350 | 2.75-3.9% |

-continued

| Ingredients | Percentage by Weight of in the Composition |
|---|---|
| Xylitol (powdered) | 38-51.2% |
| Heavy PCC Precipitated Calcium Carbonate | 5.79-7.14% |
| *Stevia* Extract | 0.01-0.45% |
| *Quillaja* Extract | 1.02-2.1% |
| Liquid Bioflavonoid Extract | 0.02-0.04% |
| Purified Water | 41-54% |

A preferred process for production of the single servings 34 of toothpaste in preformed shapes includes the following steps:
1. Heat water to between 100-160 degrees Fahrenheit.
2. Add Xylitol to the heated water and mix until completely dissolved and a clear solution remains.
3. Cool the solution to approximately 75 degrees Fahrenheit.
4. Add Citofresh and Quillaja to cooled solution and mix until completely dissolved.
5. Dry blend together Konjac, Tara Gum, Xanthan/Guar, and Polyethylene glycol.
6. Add the blended solids from Step 5 to the solution from Step 4 and mix until completely dissolved.
7. Heat the solution from step 6 to between 135-210 degrees Fahrenheit and maintain the solution within this temperature range for approximately 80 seconds.
8. Mix the heated solution for approximately 7 seconds while maintaining the heated solution between 135-210 degrees Fahrenheit.
9. Add Calcium Carbonate and blend until the mixture thickens and froths while maintaining the heated mixture within a temperature range of between 135-200 degrees Fahrenheit.
10. Pour the heated mixture into the desired mold and cover while allowing the mixture to cool to room temperature.

In a preferred embodiment, the disks 30 are disposable and designed for a single use. Ideally, each disk includes fourteen compartments 32 for storing a week's worth of single servings 34 of toothpaste (two teeth brushing sessions per day) for one individual. Alternatively, the disks 30 may be refillable for multiple uses of one disk 30.

Figure 8:
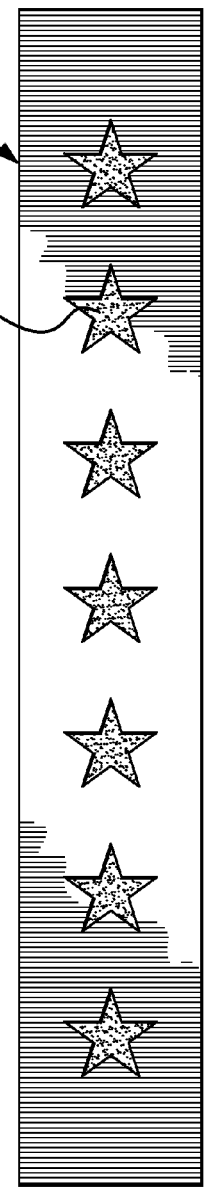
FIG. 8 is a top plan view of an alternative embodiment showing a strip that carries the preformed single servings of toothpaste in spaced compartments.

Referring to FIG. 8, an alternative embodiment is shown wherein the single servings 34 of toothpaste in preformed shapes are stored on a strip 54.

While the present invention has been shown and described in accordance with several preferred and practical embodiments, it is recognized that departures from the instant disclosure are contemplated within the spirit and scope of the present invention which are not to be limited except as defined in the following claims as interpreted under the Doctrine of Equivalents.

What is claimed is:
1. A toothpaste dispensing apparatus comprising:
   a dispensing device including a housing surrounding an interior chamber, and said housing having a dispensing opening;
   a disk having a plurality of single serving compartments arranged at spaced intervals about an outer circumferential zone of said disk, and said disk being sized for removeable insertion within the interior chamber of the dispensing device;
   a plurality of single servings of toothpaste in preformed shapes each stored in a corresponding one of said plurality of single serving compartments, each of said plurality of single servings of toothpaste being sized for removal through said dispensing opening of said housing;
   a disk advancing mechanism structured and disposed for partially rotating said disk within said interior chamber such that a next successive one of said plurality of single serving compartments is exposed through said dispensing opening; and
   a button on said dispensing device, said button normally disposed in a relaxed, raised position, and said button being structured and disposed to be depressed by application of an external force to drivingly operate said disk advancing mechanism.
2. The toothpaste dispensing apparatus as recited in claim 1 wherein said housing of said dispensing device comprises:
   an upper component and a lower component, and wherein said upper and lower components are at least partially separable from one another to allow placement of said disk within said interior chamber of said dispensing device.
3. The toothpaste dispensing apparatus as recited in claim 1 wherein said button is structured to return to the relaxed, raised position upon removal of the external depressing force.

* * * * *